US007993927B2

(12) United States Patent
Frangioni

(10) Patent No.: US 7,993,927 B2
(45) Date of Patent: Aug. 9, 2011

(54) HISTOLOGY METHODS

(75) Inventor: John V. Frangioni, Wayland, MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 1070 days.

(21) Appl. No.: 11/824,915

(22) Filed: Jul. 3, 2007

(65) Prior Publication Data

US 2008/0073566 A1 Mar. 27, 2008

Related U.S. Application Data

(60) Provisional application No. 60/818,399, filed on Jul. 3, 2006.

(51) Int. Cl.
*G01N 33/48* (2006.01)

(52) U.S. Cl. .......... 436/63; 436/164; 436/172; 436/176; 436/808; 435/40.5; 435/40.52

(58) Field of Classification Search .................... 436/63, 436/164, 172, 176, 808; 435/40.5, 40.52
See application file for complete search history.

(56) References Cited

U.S. PATENT DOCUMENTS

| 5,453,505 | A | 9/1995 | Lee et al. |
| 7,776,529 | B2 * | 8/2010 | Dallwig et al. ................. 435/6 |
| 2006/0083678 | A1 | 4/2006 | Frangioni et al. |

FOREIGN PATENT DOCUMENTS

| WO | WO 96/17628 | 6/1996 |
| WO | WO 98/22146 | 5/1998 |
| WO | WO 98/48838 | 11/1998 |
| WO | WO 98/48846 | 11/1998 |
| WO | WO 02/098885 | 12/2002 |

OTHER PUBLICATIONS

Parungo et al., "Intraoperative identification of esophageal sentinel lymph nodes with near-infrared fluorescence imaging", J. Thorac. Cardiovasc. Surg., Apr. 2005; 129: 84.*
Kim et al., "Near-infrared fluorescent type II quantum dots for sentinel lymph node mapping", Nature Biotechnology 22, 93-97 (Jan. 1, 2004).*
Brinkley, "A Brief Survey of Methods for Preparing Protein Conjugates with Dyes, Haptens, and Cross-Linking Reagents", Perspectives in Bioconjugate Chemistry, pp. 59-70, C. Meares (Ed.), ACS Publication, Washington, D.C. (1993).
Frangioni, J.V., "In vivo near-infrared fluorescence imaging", Curr. Opin. Chem. Biol., 7:626-634 (2003).
Hilger et al., "Near-infrared fluorescence imaging of HER-2 protein over-expression in tumour cells", Eur. Radiol., 14:1124-1129 (2004).
Li et al., "Tumor Localization Using Fluorescence of Indocyanine Green (ICG) in rat models", SPIE, 2389:789-797 (1995).
Licha et al., "Synthesis and characterization of cyanine dyes as contrast agents for near-infrared imaging", SPIE, 2927:192-198 (1996).
Lim et al., "Selection of quantum dot wavelengths for biomedical assays and imaging", Mol. Imaging, 2:50-64 (2003).

(Continued)

*Primary Examiner* — Jill Warden
*Assistant Examiner* — Monique Cole
(74) *Attorney, Agent, or Firm* — Fish & Richardson P.C.

(57) ABSTRACT

Described are methods of visualizing biological samples using histological staining and invisible light (e.g., infrared or near-infrared) fluorescence.

30 Claims, 1 Drawing Sheet

OTHER PUBLICATIONS

Nakayama et al., "Quantitation of brown adipose tissue perfusion in transgenic mice using near-infrared fluorescence imaging", Mol. Imaging, 2:37-49 (2003).

Ohnishi et al., "Intraoperative detection of cell injury and cell death with an 800 nm near-infrared fluorescent annexin V derivative", Am. J. Transplant., 6:2321-2331 (2006).

Ohnishi et al., "Organic Alternatives to Quantum Dots for Intraoperative Near-Infrared Fluorescent Sentinel Lymph Node Mapping", Molecular Imaging, 4:172-181 (2005).

Patonay et al., "Near-Infrared Fluorogenic Labels: New Approach to an Old Problem", Analytical Chemistry, 63:321A-327A (1991).

Riefke et al., "In vivo characterization of cyanine dyes as contrast agents for near-infrared imaging", SPIE, 2927:199-208 (1996).

Slavik, "Fluorescent Probes in Cellular and Molecular Biology", CRC Press, Inc., pp. 1-12 (1994).

Xiang et al., "Detection of Myelination Using a Novel Histological Probe", J. Histochemistry & Cytochemistry, 53:1511-1516 (2005).

Zaheer et al., "IRDye78 Conjugates for Near-Infrared Fluorescence Imaging", Molecular Imaging, 1:354-364 (2002).

Zaheer et al., "In vivo near-infrared fluorescence imaging of osteoblastic activity", Nat. Biotechnol., 19:1148-1154 (2001).

* cited by examiner

HISTOLOGY METHODS

CROSS-REFERENCE TO RELATED APPLICATIONS

This application claims priority to U.S. application Ser. No. 60/818,399, filed on Jul. 3, 2006, the entire contents of which are incorporated by reference herein.

TECHNICAL FIELD

This invention relates to methods of visualizing biological samples using histological stains and invisible light (e.g., infrared or near-infrared) fluorescence.

BACKGROUND

Histological stains can be used for the examination of cells or tissue to determine abnormalities, such as disease states. Hematoxylin and eosin are commonly used to delineate cellular structures in biological samples.

SUMMARY

This disclosure relates to the use of histological staining of cells and tissue in combination with the use of invisible light (e.g., infrared or near-infrared) fluorophores to enable visualization of a sample using both visible light and invisible light fluorescence. Also disclosed, inter alia, are biological samples containing both histological stains and invisible light fluorophores and kits for histological staining that include an invisible light fluorophore.

The invention features methods of visualizing a biological sample that include contacting a biological sample with a compound that includes an invisible light (e.g., infrared or near-infrared) fluorophore; contacting the biological sample with one or more histological stains (e.g., dyes such as hematoxylin and eosin and/or chromophoric histochemicals); visualizing the sample under visible light; and visualizing invisible light fluorescence of the sample. Visualizing the sample under visible light and visualizing infrared fluorescence can be performed separately or simultaneously. In some embodiments, one or more steps of the method are automated.

In other aspects, the invention features methods of preparing a biological sample that include contacting the biological sample with a compound that includes an invisible light (e.g., infrared or near-infrared) fluorophore, fixing the sample, and contacting the sample with one or more histological stains.

In some embodiments, the sample includes one or more of cells, tissues, blood, bone, cartilage, collagen, or other connective tissue. The sample can include eukaryotic cells and/or prokaryotic cells. In some embodiments, the sample includes cancer cells, pre-cancerous cells, or cells suspected to be cancerous or pre-cancerous. In some embodiments, the sample is an ex vivo or in vitro sample.

In some embodiments, a biological sample is isolated (e.g., biopsied) from a subject, e.g., a human, for further analysis. Preparation of the sample prior to contacting it with a composition that includes an invisible light (e.g., infrared or near-infrared) fluorophore and/or one or more histological stains can include embedding (e.g., paraffinizing), sectioning, deparaffinizing, fixing, and smearing the sample. Any sample preparation step can be performed before, during, or after contacting the sample with the compound that includes an invisible light (e.g., infrared or near-infrared) fluorophore or the histological stain. For example, the sample can be fixed following the step of contacting the sample with the composition that includes an invisible light fluorophore and prior to contacting the sample with the histological stain. In some embodiments, one or more steps of sample preparation are automated.

In some embodiments, the composition that includes an invisible light (e.g., infrared or near-infrared) fluorophore also includes a targeting ligand capable of binding (e.g., directly or indirectly) to a specific component, e.g., a component or suspected component of the sample. Exemplary targeting ligands include proteins, antibodies, and low molecular weight compounds. In some embodiments, the targeting ligand includes a member of a binding pair, e.g., a ligand-receptor pair. In some embodiments, the targeting ligand is biotin or an avidin. The invisible light fluorophore can be linked (e.g., conjugated) to the targeting ligand covalently or non-covalently. Conjugated targeting ligands can be used in immunofluorescence methods, e.g., as a secondary antibody to detect binding of a primary antibody to an antigen of interest in the sample.

Visualizing histological staining of the sample can be performed, e.g., by eye or using a microscope. In some embodiments, an image of the sample can be captured using a camera, e.g., using film, or using a charge coupled device. The capturing of one or more images of one or more samples can be automated.

Visualizing invisible light (e.g., infrared or near-infrared) fluorescence of the sample can be performed, e.g., by fluorescence microscopy. In some embodiments, an image of the sample can be captured using a camera, e.g., using film, or using a charge coupled device. The capturing of one or more images of one or more samples can be automated.

The invention also features biological samples that include a histological stain and an invisible light (e.g., infrared or near-infrared) fluorophore. In some embodiments, the invisible light fluorophore is not a conventional histology dye (e.g., methylene blue).

In further aspects, the invention features kits that include a histological stain and an invisible light (e.g., infrared or near-infrared) fluorophore. The kits can further include instructions for using the histological stain and the invisible light fluorophore in a method of visualizing a biological sample.

The new methods allow for concurrent use of histological staining and techniques such as immunofluorescence to detect specific antigens in biological samples. Since both procedures can be used on one biological sample, colocalization of components of the sample is simplified.

An "invisible light fluorophore" is a compound that emits light at wavelengths above those visible to the human eye, i.e., above 670 nm, e.g., up to 10,000 nm or up to 100,000 nm. These invisible light fluorophores do not change the appearance of histological stains, and because tissue autofluorescence at these wavelengths is generally low, detection is extremely sensitive. In some embodiments, invisible light fluorophores can also include fluorophores that are visible to the naked human eye, as long as they also fluoresce in the invisible light region.

As used herein, the term "biological sample" refers to isolated, in vitro, and ex vivo cells and/or tissues.

As used herein, the term "visualization" refers to any method used to detect, view, image, or capture an image of a biological sample by viewing the image under visible light or by detecting fluorescence emitted by the sample.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION

Figure 1:
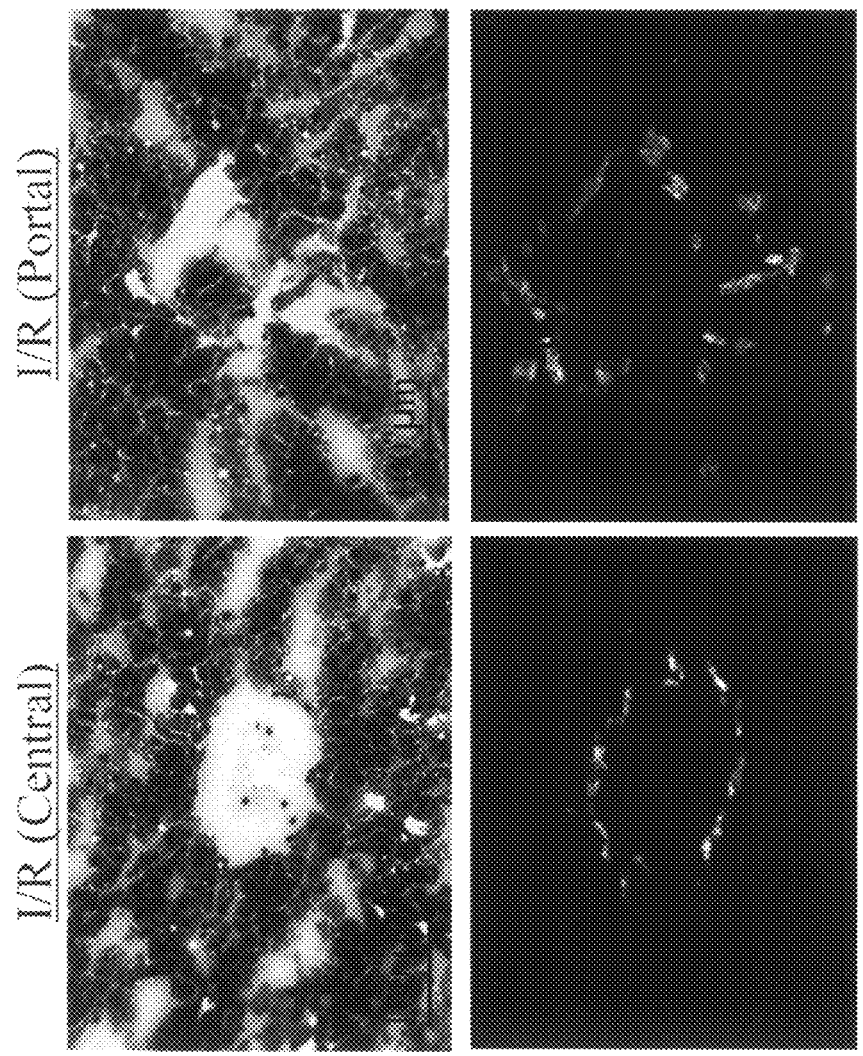
FIG. 1 is a set of micrographs depicting representative central (left) and portal (right) fields of rat liver following I/R. The top row depicts H&E staining. The bottom row depicts NIR fluorescence of the same fields.

The present invention is based, at least in part, on the surprising discovery that certain methods of histological staining do not interfere with invisible light (e.g., infrared or near-infrared) fluorophore absorption or emission, so that both staining techniques can be used concurrently on a single sample, without the invisible light fluorophore changing the appearance of the stain or vice versa. By their very nature, histological stains produce intensely colored products that absorb and reflect light of various spectra such that the stains can be distinguished from background and individual stains can be distinguished from each other. Fluorophore methods utilize molecules that absorb light of one spectrum and emit light of a different spectrum. To utilize a cytological stain in combination with a fluorophore (e.g., an infrared or near-infrared fluorophore), care should be taken to ensure that the spectra of light variously absorbed, reflected, and emitted do not significantly overlap to confound differentiation of the components from each other and differentiation of the components from endogenous tissue material. Further care should be taken to ensure that the staining and fluorescent methods are compatible with any form of fixation used. Provided herein are methods utilizing a combination of invisible light (e.g., infrared or near-infrared) fluorophores and histological stains to visualize and analyze biological samples.

Histological Staining

Numerous methods of sample preparation and histological staining are known in the art and commonly performed, e.g., to aid in research or diagnosis. See, e.g., O'Leary (ed.), 2003, *Advanced diagnostic methods in pathology: principles, practice, and protocols*, W.B. Saunders, Philadelphia; and Kiernan, 2002, *Histological and histochemical methods: theory and practice*, Arnold, London, of which the entire contents of both are incorporated herein by reference.

Specific staining techniques useful in the methods described herein include acid fast stain, alcian blue stain, alcian blue-PAS stain (PAB), hyaluronidase digestion for alcian blue alizarin stain for calcium, auramine-rhodamine stain, Bielschowsky stain, bile stain, Bodian's stain, colloidal iron stain, congo red stain, copper stain, elastic stain, elastic van Gieson stain, elastic—Weigert's resorcin-fuchsin method, modified elastic van Gieson stain, Fontana-Masson stain for melanin, melanin bleach, Fraser-Lendrum stain, Giemsa (modified May-Gruenwald) stain, Giemsa stain, Gram stain, Gridley's stain, Grimelius argyrophil Stain (Pascual's Method), Grocott's methenamine silver (GMS) Stain, hematoxylin and eosin (H&E) stain, Holzer's glial fiber stain, Hortega's pineal stain, iron stain (Prussian blue), iron stain (Turnbull's blue), Jones' silver stain, Leishman/Giemsa stain, Luxol Fast Blue (LFB) stain, Luxol Fast Blue (LFB) and cresyl violet, Methyl Green Pyronin (MGP) stain, mucicarmine stain, Nissl stain, oil red O stain, Orcein stain, osmium tetroxide, Papanicolaou stain, Periodic acid-Schiff stain (PAS), Periodic acid-Schiff, digested stain (PAS-D), phosphotungstic acid-hematoxilin (PTAH) stain, reticulin stain, Schmorl's stain, silver stain for reticulin, spirochete stain (Steiner & Steiner method), Sudan Black B stain, trichrome stain—Masson's method, trichrome Stain—microwave method, thioflavin S stain, modified thioflavin S stain, toluidine blue stain, Terminal dUTP nick end labeling (TUNEL) assay, urate crystal stain, van Gieson stain, VonKossa stain for calcium, and Wright stain.

Chromophoric histochemicals refer to compounds that create pigmented material through chemical reactions between the chemicals and components within a sample or exogenously added to the sample. A commonly performed histochemical technique is the Perls Prussian Blue reaction, used to demonstrate iron deposits in diseases like hemochromatosis.

In one non-limiting example, the methods include contacting a biological sample with a primary antibody that binds specifically to a desired antigen, washing the sample, contacting the sample with a secondary antibody conjugated to an invisible light (e.g., infrared or near-infrared) fluorophore (e.g., a fluorophore with an excitation wavelength at about 770 nm and an emission wavelength at about 800 nm, e.g., IRDye® 800CW infrared dye), fixing the sample with paraformaldehyde, and performing H&E staining.

Methods and systems for automating histological staining procedures are well known and commercially available. Exemplary systems are available from Ventana Medical Systems, Inc. (Tucson, Ariz.), Leica Microsystems Inc. (Bannockburn, Ill.), and Vision Biosystems (Norwell, Mass.).

Invisible Light Fluorophores

Any invisible light (e.g., infrared or near-infrared) fluorophores known in the art can be used in the methods and compositions described herein. Exemplary near-infrared fluorophores include dyes and other fluorophores with emission wavelengths (e.g., peak emission wavelengths) between about 680 and 1000 nm, e.g., between about 680 and 800 nm, between about 800 and 900 nm, between about 900 and 1000 nm, between about 680 and 750 nm, between about 750 and 800 nm, between about 800 and 850 nm, between about 850 and 900 nm, between about 900 and 950 nm, or between about 950 and 1000 nm. Fluorophores with emission wavelengths (e.g., peak emission wavelengths) greater than 1000 nm can also be used in the methods described herein. Exemplary fluorophores include indocyanine green (ICG), IRDye78, IRDye80, IRDye38, IRDye40, IRDye41, IRDye700, IRDye800, Cy5.5, Cy7, Cy7.5, IR-786, DRAQ5NO (an N-oxide modified anthraquinone), quantum dots, and analogs thereof, e.g., hydrophilic analogs, e.g., sulfonated analogs thereof. Commercially obtainable fluorophores include dyes such as IRDye® 78, 680, and 800CW infrared dyes (LI-COR Biotechnology, Lincoln, Nebr.), Alexa® Fluors 680, 700, and 750 (Invitrogen, Carlsbad, Calif.), and CyDye™ Fluor Cy5.5, Cy7, and Cy7.5 (GE Healthcare, Chalfont St. Giles, United Kingdom). Quantum dots with near-infrared emission can also be obtained commercially, such as Qdot® 705 and 800 nanocrystals (Invitrogen, Carlsbad, Calif.).

In some embodiments, the near-infrared fluorophore has a structure of Formula I:

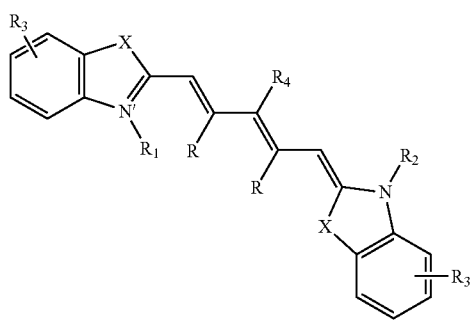

Formula I wherein, as valence and stability permit,

X represents $C(R)_2$, S, Se, O, or $NR_5$;

R represents H or lower alkyl, or two occurrences of R, taken together, form a ring together with the carbon atoms through which they are connected;

$R_1$ and $R_2$ represent, independently, substituted or unsubstituted lower alkyl, lower alkenyl, cycloalkyl, cycloalkylalkyl, aryl, or aralkyl, optionally substituted by sulfate, phosphate, sulfonate, phosphonate, halogen, hydroxyl, amino, cyano, nitro, carboxylic acid, or amide, or a pharmaceutically acceptable salt thereof;

$R_3$ represents, independently for each occurrence, one or more substituents to the ring to which it is attached, such as a fused ring, sulfate, phosphate, sulfonate, phosphonate, halogen, lower alkyl, hydroxyl, amino, cyano, nitro, carboxylic acid, or amide, or a pharmaceutically acceptable salt thereof;

$R_4$ represents H, halogen, or a substituted or unsubstituted ether or thioether of phenol or thiophenol;

$R_5$ represents, independently for each occurrence, substituted or unsubstituted lower alkyl, cycloalkyl, cycloalkylalkyl, aryl, or aralkyl, optionally substituted by sulfate, phosphate, sulfonate, phosphonate, halogen, hydroxyl, amino, cyano, nitro, carboxylic acid, amide; or a pharmaceutically acceptable salt thereof.

In some embodiments, the two occurrences of R taken together form a six-membered ring. In some embodiments, R1, R2, and one or both R3 include sulfonate.

In some embodiments, an invisible light fluorophore described herein has a quantum yield of at least about 0.0005 (e.g., at least 0.001, 0.002, 0.005, 0.010, 0.020, 0.050, 0.10, 0.20, or 0.5). The quantum yield can be either as measured in a solution or suspension of the fluorophore, or as measured in situ in a biological sample.

Many infrared and near-infrared dyes and quantum dots can be purchased pre-derivatized with one or more reactive groups, such as a N-hydroxysuccinimide (NHS) reactive group, a maleimide reactive group, an iodoacetyl reactive group, or a hydrazide reactive group. These reactive groups can be used in conjugation of the fluorophores to another molecule, e.g., a targeting ligand. Many infrared and near-infrared dyes and quantum dots can also be obtained pre-conjugated to molecules such as streptavidin and antibodies.

Methods of preparing reactive dyes and conjugating reactive dyes to biomolecules (e.g., targeting ligands) are known in the art. Several studies on the use of NIR dyes, and dye-biomolecule conjugates have been published. For example, see Patonay et al., Near-Infrared Fluorogenic Labels: New Approach to an Old Problem, *Analytical Chemistry*, 63:321A-327A (1991); Brinkley, A Brief Survey of Methods for Preparing Protein Conjugates with Dyes, Haptens, and Cross-Linking Reagents, *Perspectives in Bioconjugate Chemistry*, pp. 59-70, C. Meares (Ed), ACS Publication, Washington, D.C. (1993); Slavik, *Fluorescent Probes in Cellular and Molecular Biology*, CRC Press, Inc. (1994); Lee et al., U.S. Pat. No. 5,453,505; Hohenschuh et al., WO 98/48846; Turner et al., WO 98/22146; Kai et al., WO 96/17628; Snow et al., WO 98/48838; Ohnishi et al., Mol. Imaging, 4:172-81 (2005); and Zaheer et al., IRDye78 Conjugates for Near-Infrared Fluorescence Imaging, *Molecular Imaging*, 1(4):354-364 (2002), all of which are incorporated herein by reference.

Targeting Ligands

Specific proteins, protein fragments, peptides, antibodies, carbohydrates, or antigens that are useful as targeting ligands are described in U.S. Published Patent Application No. 2006/0083678 and WO 02/098885. A specific targeting ligand is the RGD peptide, which specifically binds to $alpha_v\beta_3$ integrin. It is known that this integrin is overexpressed by various tumors, and thus, these RGD targeting peptides enable the dyes to preferentially label tumors that overexpress these integrins. Other targeting ligands include melanocyte stimulating hormone (MSH), which targets melanoma cells, or bombesin, somatostatin, or Sandostatin™ (synthetic), which target somatostatin receptors.

A specific protein useful for conjugating to an invisible light (e.g., infrared or near-infrared) fluorophore is annexin V, which is capable of binding with high affinity to the phosphatidylserine exposed during either apoptosis or necrosis of cells. Other proteins, such as soluble receptor fusion proteins (e.g., receptor-Fc fusion proteins) can also be used in the methods described herein.

Low molecular weight ligands, e.g., peptides and small molecules, with a molecular weight of less than about 2000, e.g., 1800, 1500, 1400, 1300, 1200, 1100 or less, e.g., 1000 can be used. Specific low molecular weight targeting ligands include octreotide (Sandostatin™), β-AG, GPI-18648, and other low molecular weight peptides, e.g., aminobisphosphonates, e.g., pamidronate (Kato et al., J. Immunol., 167:5092-8, 2001).

An invisible light (e.g., infrared or near-infrared) fluorophore can also be reacted with an antibody to create conjugate agents. Specific examples of antibodies are monoclonal antibodies to 10 prostate-specific membrane antigen (PSMA), e.g., 7E11-C5.3 antibody. Typically, antibodies and antibody fragments have a molecular weight of greater than about 30,000 Daltons.

A number of antibodies against cancer-related antigens are known and/or commercially available; exemplary antibodies are described in Ross et al., Am. J. Clin. Pathol., 119:472-485, 2003.

Methods for making suitable antibodies are known in the art. A full-length antigen or antigenic peptide fragment thereof can be used as an immunogen, or can be used to identify antibodies made with other immunogens, e.g., cells, membrane preparations, and the like, e.g., E rosette positive purified normal human peripheral T cells, as described in U.S. Pat. Nos. 4,361,549 and 4,654,210.

Methods for making monoclonal antibodies are known in the art. Briefly, the process involves obtaining antibody-secreting immune cells (lymphocytes) from the spleen of a mammal (e.g., mouse) that has been previously immunized with the antigen of interest (e.g., a cancer-related antigen) either in vivo or in vitro. The antibody-secreting lymphocytes are then fused with myeloma cells or transformed cells that are capable of replicating indefinitely in cell culture, thereby producing an immortal, immunoglobulin-secreting cell line.

The resulting fused cells, or hybridomas, are cultured, and the resulting colonies screened for the production of the desired monoclonal antibodies. Colonies producing such antibodies are cloned, and grown either in vivo or in vitro to produce large quantities of antibody. A description of the theoretical basis and practical methodology of fusing such cells is set forth in Kohler and Milstein, Nature, 256:495, 1975, which is hereby incorporated by reference.

Mammalian lymphocytes are immunized by in vivo immunization of the animal (e.g., a mouse) with a cancer-related antigen. Such immunizations are repeated as necessary at intervals of up to several weeks to obtain a sufficient titer of antibodies. Following the last antigen boost, the animals are sacrificed and spleen cells removed.

Fusion with mammalian myeloma cells or other fusion partners capable of replicating indefinitely in cell culture is effected by known techniques, for example, using polyethylene glycol ("PEG") or other fusing agents (See Milstein and Kohler, Eur. J. Immunol. 6:511 (1976), which is hereby incorporated by reference). This immortal cell line, which is preferably murine, but can also be derived from cells of other mammalian species, including but not limited to rats and humans, is selected to be deficient in enzymes necessary for the utilization of certain nutrients, to be capable of rapid growth, and to have good fusion capability. Many such cell lines are known to those skilled in the art, and others are regularly described.

Procedures for raising polyclonal antibodies are also known. Typically, such antibodies can be raised by administering the protein or polypeptide of the present invention subcutaneously to New Zealand white rabbits that have first been bled to obtain pre-immune serum. The antigens can be injected at a total volume of 100 µl per site at six different sites. Each injected material will contain synthetic surfactant adjuvant pluronic polyols, or pulverized acrylamide gel containing the protein or polypeptide after SDS-polyacrylamide gel electrophoresis. The rabbits are then bled two weeks after the first injection and periodically boosted with the same antigen three times every six weeks. A sample of serum is then collected 10 days after each boost. Polyclonal antibodies are then recovered from the serum by affinity chromatography using the corresponding antigen to capture the antibody. Ultimately, the rabbits are euthanized, e.g., with pentobarbital 150 mg/Kg IV. This and other procedures for raising polyclonal antibodies are disclosed in E. Harlow, et. al., editors, *Antibodies: A Laboratory Manual* (1988).

In addition to utilizing whole antibodies, the invention encompasses the use of binding portions of such antibodies. Such binding portions include F(ab) fragments, F(ab')$_2$ fragments, and Fv fragments. These antibody fragments can be made by recombinant methods or conventional procedures, such as proteolytic fragmentation procedures, as described in J. Goding, *Monoclonal Antibodies: Principles and Practice*, pp. 98-118 (N.Y. Academic Press 1983).

Examples of immunologically active portions of immunoglobulin molecules include F(ab) and F(ab')$_2$ fragments, which retain the ability to bind antigen. Such fragments can be obtained commercially, or using methods known in the art. For example F(ab')$_2$ fragments can be generated by treating the antibody with an enzyme such as pepsin, a non-specific endopeptidase that normally produces one F(ab')$_2$ fragment and numerous small peptides of the Fc portion. The resulting F(ab')$_2$ fragment is composed of two disulfide-connected F(ab) units. The Fc fragment is extensively degraded and can be separated from the F(ab)$_2$ by dialysis, gel filtration, or ion exchange chromatography. F(ab) fragments can be generated using papain, a non-specific thiol-endopeptidase that digests IgG molecules, in the presence of a reducing agent, into three fragments of similar size: two Fab fragments and one Fc fragment. When Fc fragments are of interest, papain is the enzyme of choice, because it yields a 50,00 Dalton Fc fragment. To isolate the F(ab) fragments, the Fc fragments can be removed, e.g., by affinity purification using protein A/G. A number of kits are available commercially for generating F(ab) fragments, including the ImmunoPure™ IgG1 Fab and F(ab')$_2$ Preparation Kit (Pierce Biotechnology, Rockford, Ill.). In addition, commercially available services for generating antigen-binding fragments can be used, e.g., Bio Express, West Lebanon, N.H.

The antibody can also be a single chain antibody. A single-chain antibody (scFV) can be engineered (see, for example, Colcher et al., Ann. N.Y. Acad. Sci. 880:263-80, 1999; and Reiter, Clin. Cancer Res. 2:245-52, 1996). The single chain antibody can be dimerized or multimerized to generate multivalent antibodies having specificities for different epitopes of the same target protein. In some embodiments, the antibody is monovalent, e.g., as described in Abbs et al., Ther. Immunol. 1(6):325-31, 1994, incorporated herein by reference.

Purification of Conjugates

Following conjugation, unreacted invisible light fluorophores can be separated from conjugates. Typical means for separation include chromatography (e.g., HPLC, gel filtration chromatography, or affinity chromatography) and ultrafiltration. Methods of separation unreacted fluorophores are well-known to those of skill in the art.

Visualizing Invisible Light Fluorescence

Methods of detecting, visualizing, and imaging invisible light (e.g., infrared or near-infrared) fluorescence are known. See, e.g., Zaheer et al., Nat. Biotechnol., 19:1148-1154, 2001; and Nakayama et al., Mol. Imaging, 2:37-49, 2003. Systems for visualizing invisible light fluorescence are available commercially, such as the Odyssey® Infrared Imaging System (LI-COR Biotechnology, Lincoln, Nebr.).

Kits

The present invention is also directed to kits that include one or more histological stains and a composition comprising a near-infrared fluorophore. The kits are useful, e.g., for performing the methods described herein.

The exact nature of the components configured in the inventive kit depends on its intended purpose. For example, the histological stain can include one or more reagents required to perform a particular cytological staining method, e.g., a method described herein. Similarly, the composition comprising a near-infrared fluorophore can be selected to include, e.g., a targeting ligand so as to visualize a particular cell or cellular component.

Instructions for use may be included in the kit. "Instructions for use" typically include a tangible expression describing the technique to be employed in using the components of the kit to effect a desired outcome, such as the method of using the components to visualize a sample.

Optionally, the kit also contains other useful components, such as, diluents, buffers, fixatives, applicators, pipetting or measuring tools, or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well known methods, preferably to provide a sterile, contaminant-free environment. The packaging materials employed in the kit are those customarily utilized in vaccinations or cancer treatments As used herein, the term "package" refers to a suitable solid matrix or material such as glass, plastic, paper, foil, and the like, capable of holding the individual kit components. Thus, for example, a package can be a glass vial used to contain suitable quantities of an inventive composition containing for example, dendritic cell vaccines as described above.

EXAMPLE

In this example, we prepare a NIR fluorescent annexin V derivative, and show simultaneous staining of a tissue section with NIR fluorescent annexin and H&E. The example is for illustration only and is not meant to limit the invention in any way.

Materials and Methods

Reagents

The N-hydroxysuccinimide (NHS) ester (CW800-NHS) and carboxylic acid (CW800-CA) forms of IRDye™ 800CW NIR dye were provided as dry powders from LI-COR (Lincoln, Nebr.). They were resuspended at 30 mM in dimethylsulfoxide (DMSO; Sigma, St. Louis, Mo.) under reduced light conditions and stored at −80° C. Etoposide was purchased from Sigma. Annexin V, 10 mg/ml in phosphate-buffered saline (PBS), pH 7.4, was from Theseus Imaging Corporation (Boston, Mass.) and was stored at 4° C. Terminal dUTP nick end labeling (TUNEL) assay was performed using a Dead End™ Fluorometric TUNEL System (Progema, Madison, Wis.).

Conjugation Reactions

All steps were performed under reduced light conditions. Reactions contained 5 mg/ml annexin V and various molar ratios of CW800-NHS in phosphate buffered saline (6 mM phosphate, 150 mM NaCl, pH 7.8; PBS) with total reaction volumes ranging from 100 µL (analytical) to 5 ml (preparative). Conjugation was initiated by adding CW800-NHS, and constant agitation (without frothing) was continued for 2 hours at RT. Quenching of unreactive NHS esters was not necessary given the purification system used.

Gel-Filtration Chromatography

The gel-filtration chromatography system consisted of an ÄKTA™ prime pump with fraction collector (Amersham Biosciences, Piscataway, N.J.) and Econo-Pac™ P6 chromatographic cartridge with a cut-off of 6,000 Da (Bio-Rad, Hercules, Calif.). Gel-filtration, and on-line absorbance and fluorescence spectrometry was performed as described in detail previously (Ohnishi et al., Mol. Imaging, 4:172-181, 2005). After conjugation, the sample was loaded into the injector and run at a flow rate of 1 ml/min using PBS, pH 7.8 as mobile phase. Full spectrum absorbance and fluorescence data were recorded every 10 seconds. Desired products were collected by the fraction collector, pooled, and stored at 4° C. in the dark without preservatives until use. Average yield was 80% or greater. The labeling ratio and the concentration of the conjugated protein (annexin800) were estimated using the extinction coefficients of annexin V ($\epsilon_{280nm}$=38,800 M$^{-1}$ cm$^{-1}$) and CW800-CA ($\epsilon_{777nm}$=289,000 M$^{-1}$ cm$^{-1}$) in 20% methanol in PBS, with correction for the 6.5% of measured absorbance at 280 nm due to CW800-CA:

$$\text{Labeling Ratio} = (Abs_{777nm}/\epsilon_{777nm})/((Abs_{280nm} - 0.065 * Abs_{777nm})/\epsilon_{280nm})$$

MALDI-TOF Mass Spectrometry

Molecular weights of intact annexin V and annexin800 were measured using MALDI-TOF mass spectrometry on a Voyager-DE (Applied Biosystems, Foster City, Calif.) as previously described (Ohnishi et al., Mol. Imaging, 4:172-181, 2005). One µg of protein in PBS, pH 7.8 was desalted with a ZipTip™ C4 pipette tip (Millipore, Billerica, Mass.), equilibrated with 100% acetonitrile, 50% acetonitrile with 0.05% trifluoroacetic acid (TFA), and 0.1% TFA sequentially. Samples were loaded with the matrix 3,5-dimethoxy-4-hydroxycinnamic acid (sinapinic acid), and the mass spectrum was obtained from 100 shots using positive reflector mode and a laser intensity of 2600-2800V, with a spectral range of 30,000-50,000 Da. Data were analyzed with Data Explorer (Applied Biosystems) software.

ES-TOF Mass Spectroscopic Site Mapping

230 µL of 8 M urea/400 mM ammonium bicarbonate solution was added to 500 µg annexin V or annexin800 in 20 µL of PBS, pH 7.8. 5 µL of 45 mM dithiothreitol (DTT) was added and incubated for 15 min at 50° C. 5 µL of 100 mM iodoacetamide was added and incubated for 15 minutes at RT. The mixture was diluted with 750 µL of buffer (80 mg ammonium bicarbonate and 6 mg CaCl$_2$ in 10 ml H$_2$O), 20 µg of TPCK-trypsin (L-1-tosylamide-2-phenylethyl ketone-treated, Sigma) in H$_2$O was added, and the solution was incubated for 24 hours at 37° C. 20 µL of this peptide digest was used for analysis on a Waters (Milford, Mass.) LCT ES-TOF LC/MS equipped with dual wavelength absorbance detector (Waters), multi-wavelength fluorescence detector (Waters), a Sedex Model 75 evaporative light scatter detector (ELSD; Richards Scientific, Novato, Calif.), and a lock-spray.

The absorbance detector was set to 254 and 700 nm (the maximum permitted wavelength), and fluorescence detector was set to excite at 770 nm and detect emission at 800 nm. Leucine enkephalin (0.5 ng/µL) was used as a mass reference. Buffer A was 10 mM triethylammonium acetate, pH 7 (Glen Research, Sterling, Va.) and buffer B was acetonitrile. Peptides were resolved on a 2.1×150 mm Symmetry C$_{18}$ column (Waters) at a flow rate of 0.3 ml/min, using a gradient of 5% to 40% B over 35 minutes. Mass was measured in ES+ mode. Data were analyzed with MassLynx (Waters) software, and expected peptide masses were calculated from the mass obtained from Peptidemass online with the addition of the mass of CW800-CA (1003.24) and subtraction of the mass of H$_2$O (18.02). 3-D protein structure was visualized on a Macintosh iMac™ computer running RasMac™ Molecular Graphics software version 2.6-ucb1.0 (University of California, Berkeley, Calif.).

Biopotency of Annexin800

Biopotency of fresh (prepared the same day) and stored (4° C. in the dark for 3 months) annexin800 (labeling ratio=1.2) was measured using a Biacore® 2000 (Biacore AB, Uppsala, Sweden; (Malmqvist, Biochem. Soc. Trans., 27:335-340, 1999)), equipped with a L1 sensor chip coated with phosphatidylserine (PS), or phosphatidylcholine (PC) as a control (Vanderheyden et al., Nucl. Med. Biol., 33:135-144, 2006). The samples were mixed in 50 mM HEPES, pH 7.4 and 100 mM NaCl containing varying calcium concentrations. The equilibrium value of specific annexin-membrane binding at each calcium concentration was measured as the change in resonance units (RUs) seen on the PS chip subtracting the change observed on the PC chip. Relative RU was calculated with the maximum RU as 1.0. EC$_{50}$ was determined by fitting the titration data to a model of equilibrium binding to homogenous sites.

Intraoperative Cell Injury and Death Detection

Animals were housed in an AAALAC-certified facility and were studied under the supervision of an approved institutional protocol. 300-350 g Wistar male rats were purchased from Charles River Laboratories (Wilmington, Mass.). All animals acclimated to the animal facility for at least 48 hours prior to experimentation, and were euthanized after experimentation using pentobarbital (rats).

For ischemia/reperfusion (I/R) of rat liver, the right hepatic artery and corresponding portal vein were clamped with a surgical clip (Roboz, Gaithersburg, Md.) for 1 hour, and reperfused for 2 hours. For I/R of rat intestine, a branch artery of the superior mesenteric artery and its corresponding vein, and both sides of the occupying intestine, were clamped for 1 hour with a surgical clip (Roboz) and mosquito clamp, respectively, and reperfused for 2 hours. After intravenous injection of 1.2 mg/kg annexin800 protein (labeling ratio=1.2; 40 nmol/kg of fluorophore total), signal to background ratio (SBR) was measured every minute over the course of 60 minutes. The background region of interest was abdominal wall for liver I/R, and skin for intestinal I/R.

Histopathology and Immunofluorescence Microscopy

Tissue sections from I/R and normal areas were placed in histology cassettes and embedded in Tissue-Tek® O.C.T. compound (Sakura Finetek USA, Torrance, Calif.), and frozen immediately in liquid nitrogen. Sections were stained by hematoxylin and eosin (H&E). For each microscope field an H&E image under brightfield light and a 800 nm NIR fluorescence image was obtained using a on a four-channel microscope as described previously (Nakayama et al., Mol. Imaging, 2:37-49, 2003).

Synthesis and Optical Properties of Annexin800

After reaction with fluorophore, annexin800 was successfully separated from free NHS ester and free CW800-CA, with a purity of >98% by gel-filtration. Annexin800 absorbance showed a prominent peak at 700 nm in PBS that decreased in the presence of methanol, suggesting dye aggregation in PBS. The absorbance and emission peaks of annexin800 were 777 nm and 797 nm, respectively. As expected, the labeling ratio increased as the mixing ratio increased. However, as the labeling ratio increased, the per-fluorophore fluorescence decreased and the per-molecule fluorescence peaked. Due to this phenomenon, it was concluded that maximal per-molecule fluorescence yield occurs at a labeling ratio of 1.2. MALDI-TOF mass spectrometry confirmed that annexin800 is a mixture of annexin V substituted with various numbers of CW800, and validated the accuracy of the calculation of labeling ratio from the absorbance scan.

Identification of Fluorophore Location(s) on Annexin800

In order to determine the conjugation site(s) of CW800, we performed tryptic mass-spec fingerprinting. The total ion chromatogram (TIC) demonstrated that peptides from both annexin V and annexin800 were well separated, with a small number of peaks of 700 nm absorbance (the highest available wavelength on our detector) and 800 nm fluorescence were observed from annexin800, but not from annexin V (data not shown). By measuring the mass of the peptides with 700 nm absorbance and 800 nm fluorescence, we obtained two binding sites. Based on the crystal structure of annexin V (Huber et al., EMBO J., 9:3867-3874, 1990), each substitution site is at the surface of the protein, and fluorophores are located relatively close to each other, but away from the calcium binding sites that are required for PS binding.

Biopotency of Annexin800

The biopotency of calcium-dependent, annexin800 binding to PS was quantified using surface plasmon resonance. Annexin V and annexin800 (labeling ratio=1.2) had similar binding capacities to PS. Indeed, the $EC_{50}$ for calcium-dependence was 0.28 mM and 0.21 mM, for annexin V and annexin800, respectively. After 3 months of storage of annexin800 in the dark at 4° C., there was no change in potency ($EC_{50}$=0.27 mM). The fluorescence emission of annexin800 decreased only 8% over this same time.

Simultaneous H&E and NIR Fluorescence Histology

After 1 hour of ischemia and 2 hours of reperfusion of the right lobes of the rat liver, annexin800 protein (labeling ratio=1.2) was injected intravenously as described in Materials and Methods. Sufficient background clearance occurred within 10 minutes in the liver to provide the surgeon with optical imaging of cell injury and death. Injection of the same concentration of CW800-CA resulted in no difference in dye accumulation between I/R and normal liver, no vascular leakage, and no evidence of infarction. The SBR of the I/R liver increased immediately after injection of annexin800 and rose to 5.2 at 60 minutes, while the SBR of uninjured liver remained relatively constant at ≈2.0 and increased only slightly as background NIR fluorescence was cleared.

Samples of rat liver were fixed as described above, stained with H&E, and visualized under both brightfield and NIR fluorescence. The results, shown in FIG. 1 show clearly that: 1) NIR fluorescence does not alter the appearance of the H&E stain, 2) the H&E stain does not alter the appearance of the NIR fluorescence, and 3) a simple fluorescence microscope can be used to visualize typical histology (H&E using brightfield) and location of the annexin V protein of interest (NIR fluorescence) on the same tissue slice.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of visualizing a biological sample, the method comprising:
    (a) contacting a biological sample with a composition comprising a near-infrared fluorophore;
    (b) contacting the biological sample with one or more histological stains;
    (c) visualizing the sample under visible light; and
    (d) visualizing near-infrared fluorescence of the sample.

2. The method of claim 1, wherein the sample comprises one or more of cells, tissue, blood, bone, cartilage, and collagen.

3. The method of claim 2, wherein the sample comprises eukaryotic cells.

4. The method of claim 2, wherein the sample comprises cancer cells or pre-cancerous cells.

5. The method of claim 2, wherein the sample comprises prokaryotic cells.

6. The method of claim 1, wherein the sample is prepared by one or more of fixing, embedding, sectioning, and smearing.

7. The method of claim 1, further comprising fixing the biological sample after (a) and prior to (b).

8. The method of claim 1, wherein the one or more histological stains comprise one or more dyes.

9. The method of claim 8, wherein the one or more dyes are hematoxylin and eosin.

10. The method of claim 1, wherein the one or more histological stains comprise one or more chromophoric histochemicals.

11. The method of claim 1, wherein the composition comprises a targeting ligand capable of binding to a specific component.

12. The method of claim 11, wherein the composition comprises a targeting ligand capable of binding directly to the specific component.

13. The method of claim 11, wherein the composition comprises a targeting ligand capable of binding indirectly to the specific component.

14. The method of claim 11, wherein the composition comprises an antibody.

15. The method of claim 11, wherein the composition comprises a member of a binding pair.

16. The method of claim 15, wherein the binding pair comprises biotin and an avidin.

17. The method of claim 15, wherein the binding pair comprises a ligand and a receptor of said ligand.

18. The method of claim 13, wherein the composition is conjugated to a near-infrared fluorophore.

19. The method of claim 1, wherein the near-infrared fluorophore comprises a cyanine dye.

20. The method of claim 1, wherein the composition comprises IRDye®800CW infrared dye.

21. The method of claim 1, wherein the composition comprises a quantum dot.

22. The method of claim 1, wherein visualizing comprises the use of a microscope.

23. The method of claim 1, wherein visualizing comprises the use of a camera.

24. The method of claim 23, wherein the camera comprises film.

25. The method of claim 1, wherein visualizing comprises the use of a charge coupled device.

26. The method of claim 1, wherein one or more of the steps is automated.

27. A kit comprising one or more histological stains and a composition comprising a near-infrared fluorophore, said kit further comprising instructions to use the components of the kit in a method of visualizing a biological sample according to claim 1.

28. The method of claim 1 wherein the visualizing of steps (c) and (d) is carried out simultaneously.

29. The method of claim 28 wherein the simultaneous visualizing comprises the use of a microscope.

30. The method of claim 29 wherein the simultaneous visualizing comprises capturing an image of the sample.

* * * * *